United States Patent [19]

Svenson et al.

[11] Patent Number: 5,154,501
[45] Date of Patent: Oct. 13, 1992

[54] PROCESS FOR IDENTIFICATION OF AN ACTIVE SITE OF VENTRICULAR TACHYCARDIA AND FOR ELECTRODE ATTACHMENT OF AN ENDOCARDIAL DEFILBRILATOR

[75] Inventors: Robert H. Svenson, Charlotte, N.C.; Wendell King, North Oaks, Minn.

[73] Assignee: AngeLase, Inc., Plymouth, Minn.

[21] Appl. No.: 601,241

[22] Filed: Oct. 19, 1990

[51] Int. Cl.$^5$ .............................................. A61N 1/39
[52] U.S. Cl. .................................. 128/419 D; 128/705
[58] Field of Search ............ 128/705, 419 D; 604/21; 606/7, 32-33, 46-47

[56] References Cited

U.S. PATENT DOCUMENTS

| | | | |
|---|---|---|---|
| 4,296,755 | 10/1981 | Judell | 128/705 |
| 4,641,649 | 2/1987 | Walinsky et al. | 606/33 |
| 4,643,186 | 2/1987 | Rosen et al. | 606/33 |
| 5,000,189 | 3/1991 | Throne et al. | 128/705 |
| 5,011,483 | 4/1991 | Sleister | 606/632 |

*Primary Examiner*—William E. Kamm
*Attorney, Agent, or Firm*—Hugh D. Jaeger

[57] ABSTRACT

An electrophysiologically guided arrhythmia ablation system for ventricular tachycardia or other arrhythmias. The system includes recording the electrical activation time of various parts of the heart for locating the active site of the arrhythmia. The system has the capability of processing local myocardial electrical activation data. The process includes identification of an active site which occurs during the 20-80%, preferably 35-50%, time period of a diastolic interval. The diastolic interval is monitored by appropriate electrical connections between the heart and a monitor. A mapping device connects to the monitor which maps for indicating an active site. The active site is then a site for preferred placement of an electrode for a defibrilator.

7 Claims, 1 Drawing Sheet

PROCESS FOR IDENTIFICATION OF AN ACTIVE SITE OF VENTRICULAR TACHYCARDIA AND FOR ELECTRODE ATTACHMENT OF AN ENDOCARDIAL DEFIBRILATOR

BACKGROUND OF THE INVENTION

1. Definitions

A. VT - Ventricular tachycardia.

B. Active Site Critical site to deliver ablation energy to cure VT identified by electrical activations.

C. Diastolic - That period of time between two QRS complexes of the electrocardiogram.

D. Ablation - The delivery of destructive energy to the cardiac tissues containing the active site.

2. Field of the Invention

The present invention pertains to a medical system, and more particularly, pertains to cardiac electrophysiology, specifically, ablation of cardiac arrhythmias or modification of the electrical properties of the myocardium. The present invention is also a process for identification of an active site of origin of ventricular tachycardia and for electrode attachment of an endocardial defibrilator lead.

3. Description of the Prior Art

In existing technology, the recognition of the site of the origin of the arrhythmias and the ablation function are performed separately. For ventricular tachycardia, there has been no consensus of opinion as to what electrical activation times constitute the "site of origin". Furthermore, the ablation energy source, whether DC current shock, radio frequency, microwave, or laser, has to be separately redirected by visual means to the site of suspected origin of the arrhythmia.

Arrhythmia ablation is currently performed during open heat surgery or through catheters directed percutaneously through the heart. During the surgical approach, either a hand-held electrical mapping probe or a computerized array of electrodes acquire electrical activation data seeking the site of origin of the arrhythmia. In the percutaneous catheter based approach, a catheter with recording electrodes is positioned in the heart under fluoroscopic guidance.

Following acquisition of electrical activation data, ablation energy is then later delivered by hand-held probes or catheters either in the operating room or in the cardiac catheterizational lab.

In the prior art, the process for identification of the "site of origin" of the arrhythmia was performed with electrical recording procedures designed to map the spread of electrical activation in the heart looking for the site of earliest electrical activation (site of origin). This procedure is carried out by sequentially moving a hand-held electrical recording probe or catheter over the heart and recording the time of arrival of the electrical impulse to that location. This process turned out to be a long and tedious procedure.

Prior art mapping procedures also include a sock multiple electrode array (epicardial), a balloon endocardial electrode array, a single hand-held mapping probe, or a multiple electrode catheter (endocardial) inside a chamber of the heart. These procedures require a skilled surgeon and cardiac electrophysiologist.

The particular concern was the preferred location for an electrode for an endocardial defibrilator. It was not an easy procedure to determine the preferred placement at the active site.

The prior art mapping procedures are capable of reconstructing the spread of electrical activation in the heart, but do not in themselves identify the "active site" of the arrhythmia, can be time consuming, and are separate functions from the prior art ablation procedures.

The present invention overcomes the disadvantages of the prior art by recognizing a particular window or time zone of electrical activation during the diastolic interval of the arrhythmia where ablation energy could be delivered with a high probability for successful cure.

SUMMARY OF THE INVENTION

The general purpose of the present invention is the process for identification of the critical site to attach an electrode for an endocardial defibrilator to control cardiac arrhythmia. For ventricular tachycardia, the process involves identification of a site activating during the 20-80%, preferably 35-50% of the electrical diastolic period as referenced to the body surface electrocardiogram. The electrode can be either an endocardial electrode or an epicardial electrode as may be requested.

According to one embodiment of the present invention, there is provided a process for identification of a site or sites for attachment of an electrode for a defibrilator of diastolic activation during ventricular tachycardia including the steps of measuring the diastolic interval of a heart, mapping heart tissue for an active site, identifying the active site in the 20-80%, preferably 35-50%, time period of the diastolic interval. The electrode can be either an endocardial electrode or an epicardial electrode.

The system includes the electrical activation data generation means, whether from a hand-held mapping probe or computerized electrode array in the operating room or with an electrode catheter by percutaneous approach. The system includes recognition of the appropriate electrical markers of the active site. For ventricular tachycardia, the critical active site defined in electrical activation terms encompasses a critical window of electrical activation time within electrical diastole as viewed from the surface ECG, i.e., 20-80%, preferably 35-50%, of the time between QRS complexes of the arrhythmia. This critical window of activation timing has not previously been identified.

One significant aspect and feature of the present invention is the recognition that active sites occur during the 20-80%, preferably 35-50%, time period of a diastolic interval.

Another significant aspect and feature of the present invention is the recognition of a time zone of 160-50 milliseconds before the onset of a QRS complex in which active sites occur during VT.

A further significant aspect and feature of the present invention is that a site of origin for VT is now recognized as the active site.

Having thus described the embodiments of the present invention, it is a principal object hereof to provide a process for identification of active sites for attachment of an electrode for an endocardial defibrilator.

Objects of the present invention include knowledge of the active site of ventricular tachycardia.

BRIEF DESCRIPTION OF THE DRAWINGS

Other objects of the present invention and many of the attendant advantages of the present invention will be readily appreciated as the same becomes better understood by reference to the following detailed descrip

DESCRIPTION OF THE PREFERRED EMBODIMENTS

Figure 1:
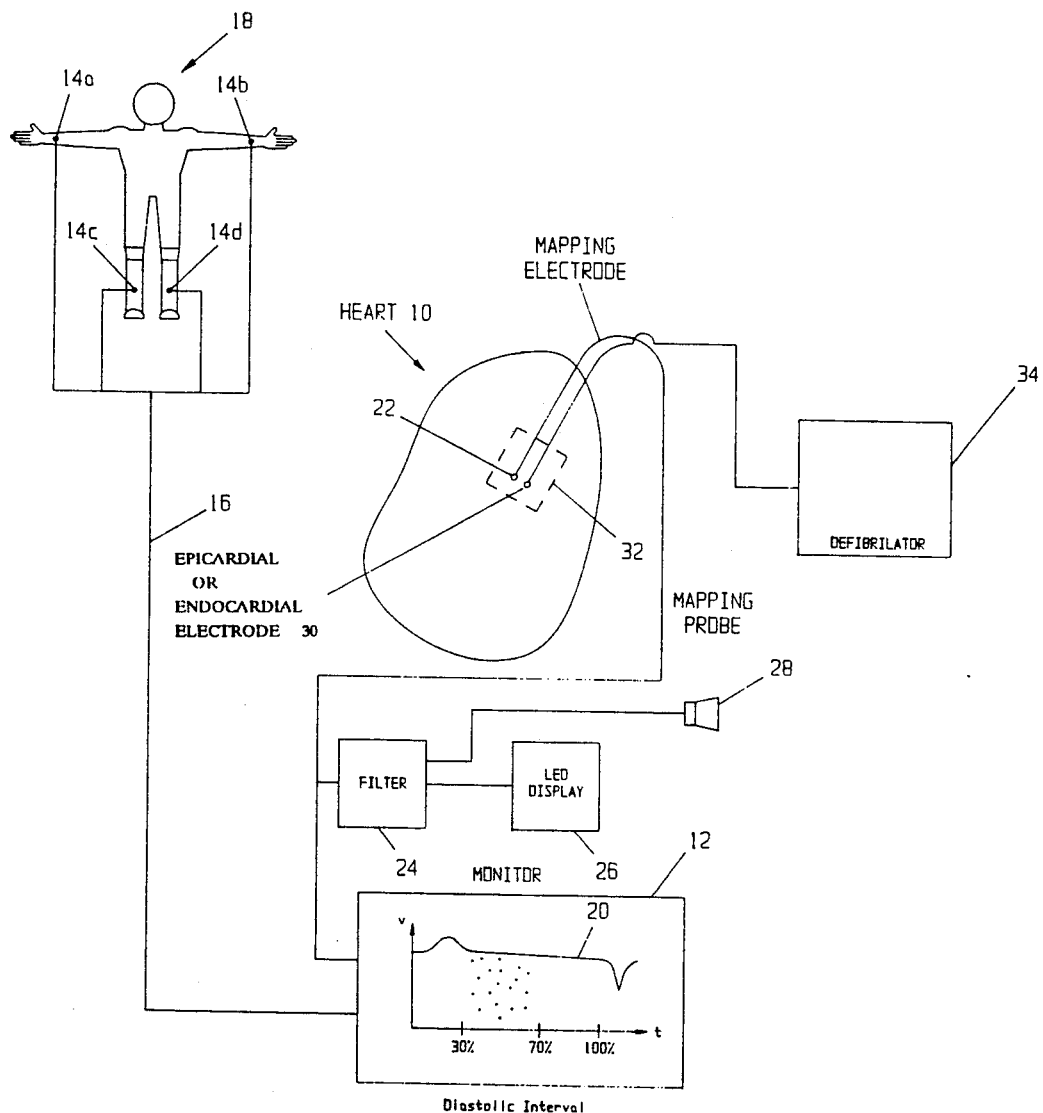
- FIG. 1 illustrates a system schematic of a process for identification of an active site and attachment of an electrode for a defibrilator.

FIG. 1 illustrates a system schematic of a process for identification of an active site including a heart 10 of a patient 18, a monitor 12, and ECG electrodes 14a-14d connected by a cable 16 from the patient 18 to the monitor 12. A mapping electrode 22 for mapping of an active site or sites also connects to the monitor 12. A display 20 is shown on the monitor 12.

A filter 24 can connect to the mapping electrode lead 22, and an illuminating display 26 such as an LED connects to the filter to indicate an active site. An electrical signaling device 28 can also connect to the filter, to indicate an active site.

Active sites are indicated between the 20-80%, preferably 35-50%, time period of the diastolic interval on the display.

Once an active site is located, the site is appropriate for placement of an electrode for a defibrilator 34. The endocardial electrode 30 can also be the mapping electrode, one in the same as illustrated in the box 32 in the dashed lines for purposes of illustration only and not to be construed or limiting of the present invention. Any suitable defibrilation can be utilized corresponding to the appropriate type of electrode.

MODE OF OPERATION

In particular, each heart beat is displayed on monitor 12. A number of consecutive beats is monitored to verify the stability of the electrical recording. After the passage of one interval for which the time period thereof is measured, a second interval begins and the appropriate window is taken. The catheter is put in place, and the signal generated indicates whether it is in the window or not. If in the window, activation of ablation energy is initiated. If not in the window, the device is moved until in the window.

The steps for the process of identification of an active site for VT and for attachment of an electrode for a defibrilator are performed by appropriate medical personnel in accordance with the Description of the Preferred Embodiments. The recognition of the active sites in the preferred 35-50% window or broadly, the 20-80% window, of the diastolic is the present invention. The teachings of the present invention can be utilized for either an endocardial electrode or an epicardial electrode for a defibrilator.

Various modifications can be made to the present invention without departing from the apparent scope hereof.

We claim:

1. Process for identification of an active site of diastolic activation during ventricular tachycardia (VT) and attachment of an electrode thereto for a defibrilator comprising the steps of:
   a. measuring the time period of a diastolic interval of a heart;
   b. mapping heart tissue for an active site;
   c. identifying the active site in the 20-80% time period of said measured time period of said diastolic interval; and,
   d. attaching an electrode at the active site for a defibrilator.

2. Process of claim 1 wherein said heart tissue is endocarial tissue, and wherein said electrode is an endocardial electrode.

3. Process of claim 1 wherein said heart tissue is epicardial tissue, and wherein said electrode is an epicardial electrode.

4. Process for identification of an active site of diastolic activation during ventricular tachycardia (VT) and attachment of an electrode thereto for a defibrilator comprising the steps of:
   a. measuring the time period of a diastolic interval of a heart;
   b. mapping heart tissue for an active site;
   c. identifying the active site in the 20-80% time period of said measured time period of said diastolic interval;
   d. attaching an electrode at the active site for a defibrilator; and
   e. attaching said endocardial defibrilator to said electrode.

5. Process of claim 4 wherein said range is 35-50%.

6. Process for identification of an active site of diastolic activation during ventricular tachycardia (VT) and attachment of an electrode thereto for a defibrilator comprising the steps of:
   a. measuring the time period of a diastolic interval of a heart;
   b. mapping heart tissue for an active site with a mapping electrode;
   c. identifying the active site in the 35-50% time period of said measured time period of said diastolic interval; and,
   d. attaching an electrode at the active site for an endocardial defibrilator.

7. Process of claim 6 wherein said endocardial electrode is also said mapping electrode.

* * * * *

UNITED STATES PATENT AND TRADEMARK OFFICE
CERTIFICATE OF CORRECTION

PATENT NO.  : 5,154,501
DATED       : Oct. 13, 1992
INVENTOR(S) : Svenson et al.

It is certified that error appears in the above-identified patent and that said Letters Patent is hereby corrected as shown below:

Column 4, line 35 delete the word "a" and substitute therefor --an endocardial--.

Signed and Sealed this

Eighth Day of March, 1994

Attest:

BRUCE LEHMAN

*Attesting Officer*          *Commissioner of Patents and Trademarks*